(12) United States Patent
Jong et al.

(10) Patent No.: US 9,045,793 B2
(45) Date of Patent: Jun. 2, 2015

(54) METHOD OF REGULATING THE EXPRESSION LEVEL OF SURVIVAL OF MOTOR NEURON 1

(75) Inventors: Yuh-Jyh Jong, Kaohsiung (TW); Shih-Hsien Hsu, Kaohsiung (TW); Jan-Gowth Chang, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 586 days.

(21) Appl. No.: 13/032,846

(22) Filed: Feb. 23, 2011

(65) Prior Publication Data

US 2012/0214860 A1 Aug. 23, 2012

(51) Int. Cl.
| | | |
|---|---|---|
| *A61K 31/404* | (2006.01) | |
| *C12Q 1/37* | (2006.01) | |
| *A61K 31/7105* | (2006.01) | |
| *G01N 33/50* | (2006.01) | |
| *G01N 33/68* | (2006.01) | |

(52) U.S. Cl.
CPC .............. *C12Q 1/37* (2013.01); *A61K 31/404* (2013.01); *A61K 31/7105* (2013.01); *G01N 33/5044* (2013.01); *G01N 33/6896* (2013.01); *G01N 2800/28* (2013.01); *G01N 2800/2878* (2013.01)

(58) Field of Classification Search
CPC . A61K 31/404; A61K 31/7105; C12N 15/111
See application file for complete search history.

(56) References Cited

U.S. PATENT DOCUMENTS

2002/0040484 A1* 4/2002 Roch et al. .................. 800/8

OTHER PUBLICATIONS

Chen et al. (Neurology, 2010, 75:2190-2197).*
Mercuri et al. (Neurology, 2007, 68:51-55).*
Gorecki, D., (Expert Opin. Emerging Drugs, 2001, 6(2): 187-198).*
Zaiss et al., (Current Gene Therapy, 2005, vol. 5, p. 323-331).*
Thomas et al., (Nature Reviews/ Genetics, 2003, vol. 4, p. 346-358).*
Kodama et al., (Current Medicinal Chemistry, 2006, vol. 13, p. 2155-2161).*
Hsu et al. Clinica Chemica Acta vol. 411 (2010) pp. 1920-1928.*
Barry S. Russman, Spinal Muscular Atrophy: Clinical Classification and Disease Heterogeneity, Journal of Child Neurology, Aug. 2007, pp. 946-951, vol. 22, No. 8.
Mitchell R. Lunn et al., Spinal Muscular Atrophy, Lancet, 2008, pp. 2120-2133, vol. 371.
Zhihua Liu et al., Membrane-associated farnesylated UCH-L1 promotes a-synuclein neurotoxicity and is a therapeutic target for Parkinson's disease, Proc Natl Acad Sci, Mar. 24, 2009, pp. 4635-4640, vol. 106, No. 12.
Hitoshi Osaka et al., Ubiquitin carboxy-terminal hydrolase L1 binds to and stabilizes monoubiquitin in neuron, Human Molecular Genetics, 2003, pp. 1945-1958, vol. 12, No. 16.
Xiaoyi Gao et al., Genome-wide Linkage Screen in Familial Parkinson Disease Identifies Loci on Chromosomes 3 and 18, The American Journal of Human Genetics, Apr. 10, 2009, pp. 499-504, vol. 84.
Rieko Setsuie et al., The functions of UCH-L1 and its relation to neurodegenerative diseases, Neurochemistry International, 2007, pp. 105-111, vol. 51.
Bing Gong et al., Ubiquitin Hydrolase Uch-L1 Rescues B-Amyloid-Induced Decreases in Synaptic Function and Contextual Memory, Cell, Aug. 25, 2006, pp. 775-788, vol. 126.
Shih-Hsien Hsu et al., bHLH-zip Transcription Factor Spz1 Mediates Mitogen-Activated Protein Kinase Cell Proliferation, Transformation, and Tumorigenesis, Cancer Research, May 16, 2005, pp. 4041-4050, vol. 65, No. 10.
Chi-Yu Lu et al., Analysis of angiotensin II receptor antagonist and protein markers at microliter level plasma by LC-MS/MS, Journal of Pharmaceutical and Biomedical Analysis, 2009, pp. 123-128, vol. 49.
Shih-Hsien Hsu et al., Dysfunctional spermatogenesis in transgenic mice overexpressing bHLH-Zip transcription factor, Spz1, Experimental Cell Research, 2004, pp. 185-198, vol. 294.
Claudia Fallini et al., Spinal muscular atrophy: The role of SMN in axonal mRNA regulation, Brain Research 1462, 2012, pp. 81-92.
Anne Corbett et al., Drug repositioning for Alzheimer's disease, Nature Reviews Drug Discovery, Nov. 2012, pp. 833-846, vol. 11.

\* cited by examiner

*Primary Examiner* — Jon E Angell
(74) *Attorney, Agent, or Firm* — WPAT, P.C.; Anthony King

(57) ABSTRACT

The present invention relates to a method of regulating the expression level of survival of motor neuron 1 (SMN1) comprising administering to a subject in need thereof a therapeutically effective amount of ubiquitin carboxyl-terminal hydrolase L1 (UCHL1) regulator and a pharmaceutically acceptable carrier. The present invention also relates to a method of detecting enzyme activity of ubiquitin carboxyl-terminal hydrolase L1 (UCHL1) in human fibroblasts comprising detecting protein expression level of survival of motor neuron 1 (SMN1).

3 Claims, 14 Drawing Sheets
(2 of 14 Drawing Sheet(s) Filed in Color)

A pH 3          pH 10

Normal

B

Type I SMA

C

FIGURE 1
D
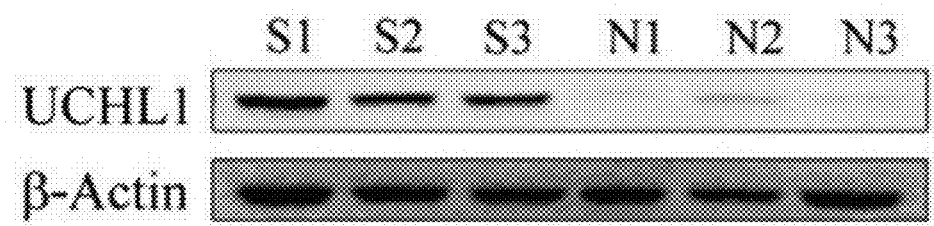
E
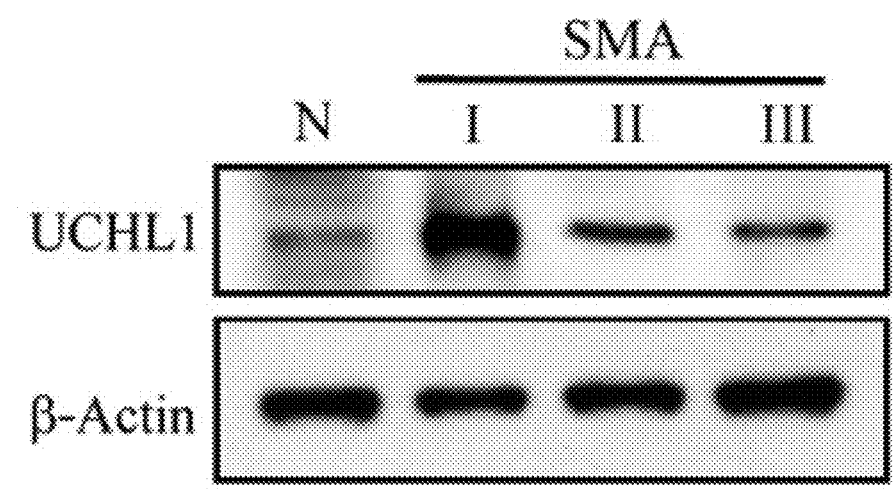

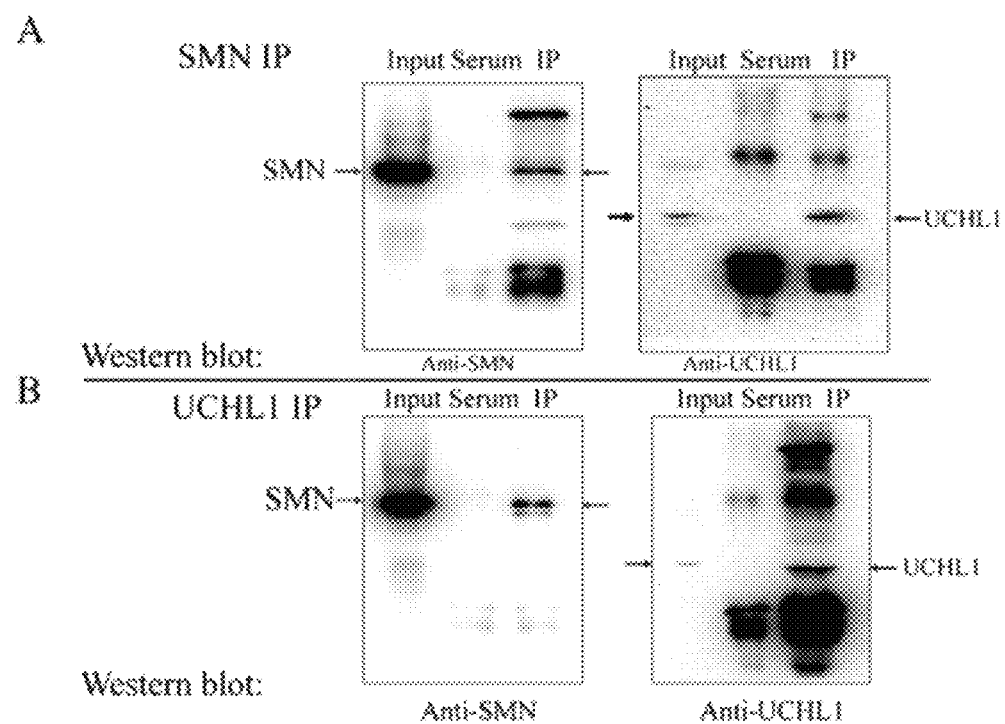

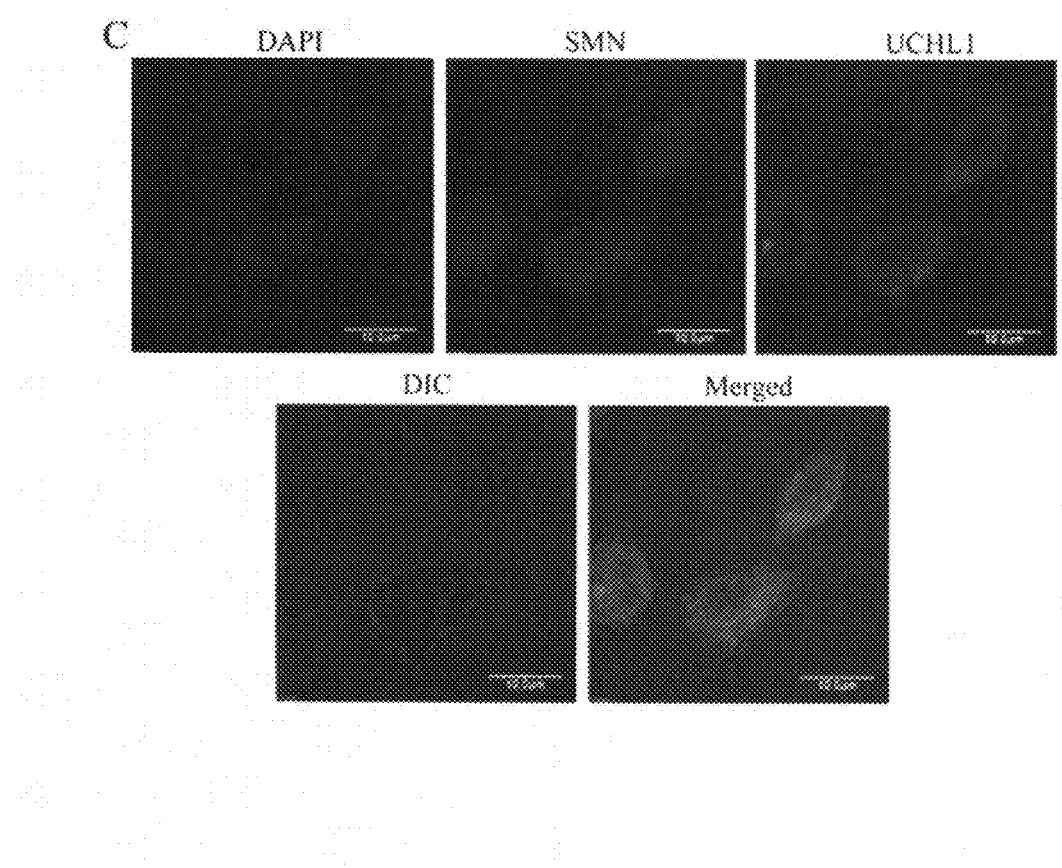

B

FIGURE 5
C
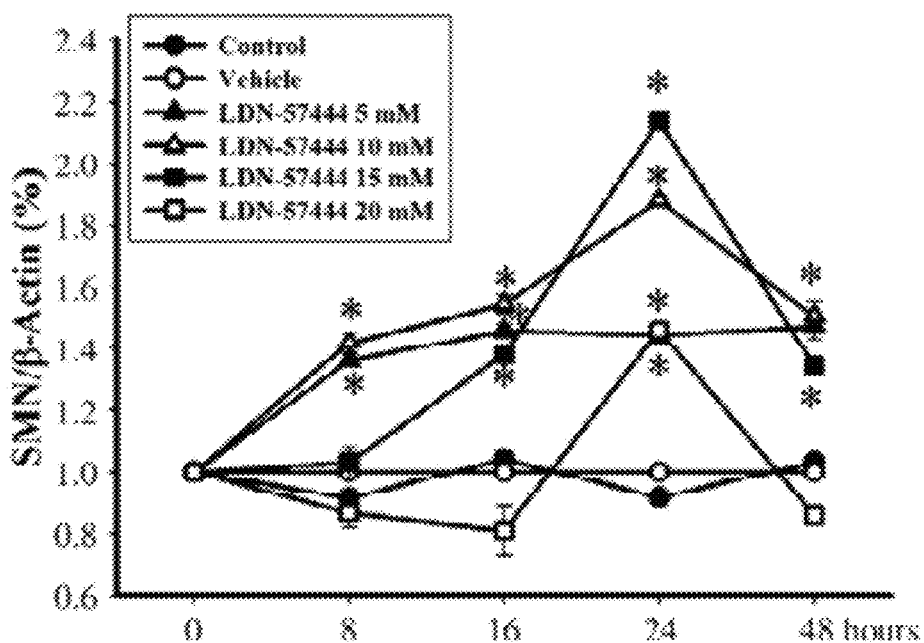
D
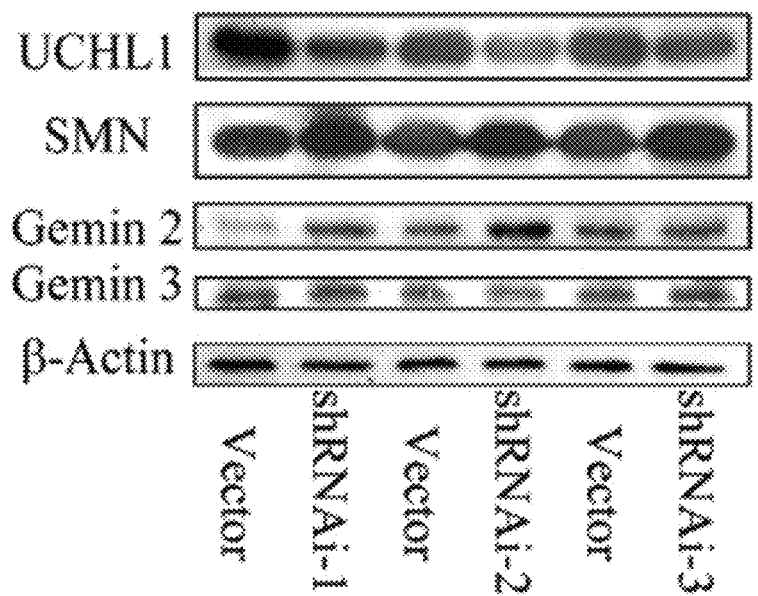

FIGURE 6
A
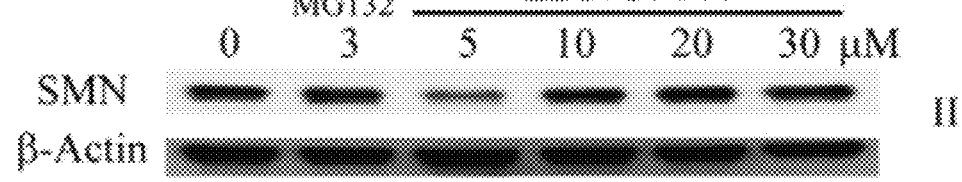
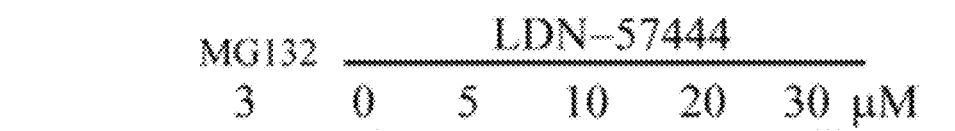
SMA

METHOD OF REGULATING THE EXPRESSION LEVEL OF SURVIVAL OF MOTOR NEURON 1

FIELD OF THE INVENTION

This invention relates to a method of regulating the expression level of survival of motor neuron 1 (SMN1). This invention also relates to a method of detecting enzyme activity of ubiquitin carboxyl-terminal hydrolase L1 (UCHL1) in human fibroblasts.

DESCRIPTION OF PRIOR ART

Proximal spinal muscular atrophy (SMA) is an autosomal recessive disease characterized by degeneration of the anterior horn cells of the spinal cord. SMA is divided into four clinical types on the basis of age of onset and motor function achieved: (1) severe type I; (2) intermediate type II; (3) mild type II; and (4) adult-onset type IV (Russman, B. S. (2007) *J Child Neurol,* 22, 946-951; Lunn, M. R. and Wang, C. H. (2008) *Lancet,* 371, 2120-2133). Two survival motor neuron (SMN) genes are typically present on chromosome 5q13: SMN1 and SMN2. Loss-of-function mutations of both copies of the telomeric gene, SMN1, are correlated with the development of SMA. The nearly identical centromeric gene SMN2, which is typically not mutated in SMA, appears to modify disease severity according to the amount of full-length (fl) SMN protein it produces, which are correlated with disease severity both in human SMA patients and SMA-like mouse model. A major issue in SMA treatment is how to increase the full length SMN protein level in SMA patients. A major advanced approach to the treatment of SMA is to augment SMN protein levels, either by preventing exon7 skipping in SMN2 transcripts or by increasing overall transcription from the SMN2 locus. To date, no cure therapy for SMA is available.

Ubiquitin carboxy-terminal hydrolase L1 (UCHL1), a 223 amino acid protein, was originally characterized as a de-ubiquitinating enzyme and recent studies indicate that it also functions as a ubiquitin (Ub) ligase (Liu, Z. et al. (2009) *Proc Natl Acad Sci USA,* 106, 4635-4640) and a mono-Ub stabilizer (Osaka, H., et al. (2003) *Hum Mol Genet,* 12, 1945-1958). It is one of the most abundant proteins in the brain (1-2% of the total soluble protein) and immunohistochemical experiments demonstrate that it is exclusively localized in neurons. Thus, its role in neuronal cell function/dysfunction was predicted. Indeed, the lack of UCHL1 expression in mice results in gracile axonal dystrophy (gad) phenotype. Down-regulation and extensive oxidative modification of UCHL1 have been observed in the brains of Alzheimer's disease (AD) patients as well as Parkinson's disease (PD) patients (Gao, X. et al. (2009) *Am J Hum Genet,* 84, 499-504; Setsuie, R. et al. (2007) *Neurochem Int,* 51, 105-111) Moreover, administration of UCHL1 was shown to alleviate the β-amyloid-induced synaptic dysfunction and memory loss associated with a mouse model of AD (Gong, B. et al. (2006) *Cell,* 126, 775-788). In addition, an isoleucine 93 to methionine amino acid mutation (I93M) of UCHL1 was identified as a cause of autosomal dominant PD. Together, all of these aspects indicate that the precise regulation of UCHL1 is essential for neurons to survive and to maintain their proper function. However, all of the activities detected in vitro are significantly lower than those of any other known Ub hydrolases, and its in vivo substrate has not yet been identified.

The present invention aimed to identify candidate proteins to distinguish SMA fibroblasts from normal fibroblasts. From 6 differentially expressed proteins, UCHL1 was identified as a key regulator in modulating the level of SMN proteins by a mechanism involving ubiquitination leading to degradation of SMN proteins. These results suggest its candidacy as a new SMA therapeutic target for new drug development or treatment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 shows the interaction between UCHL1 with SMN protein in HEK293 and NSC34 cells. (A) UCHL1 protein was detected in anti-SMN immunoprecipitate. (B) SMN protein was detected in anti-UCHL1 immunoprecipitate. (C) Immunofluorescence staining in NSC34 cells. (SMN, green; UCHL1, red; nucleus, blue (DAPI))(1,000×)

SUMMARY OF THE INVENTION

Figure 1:
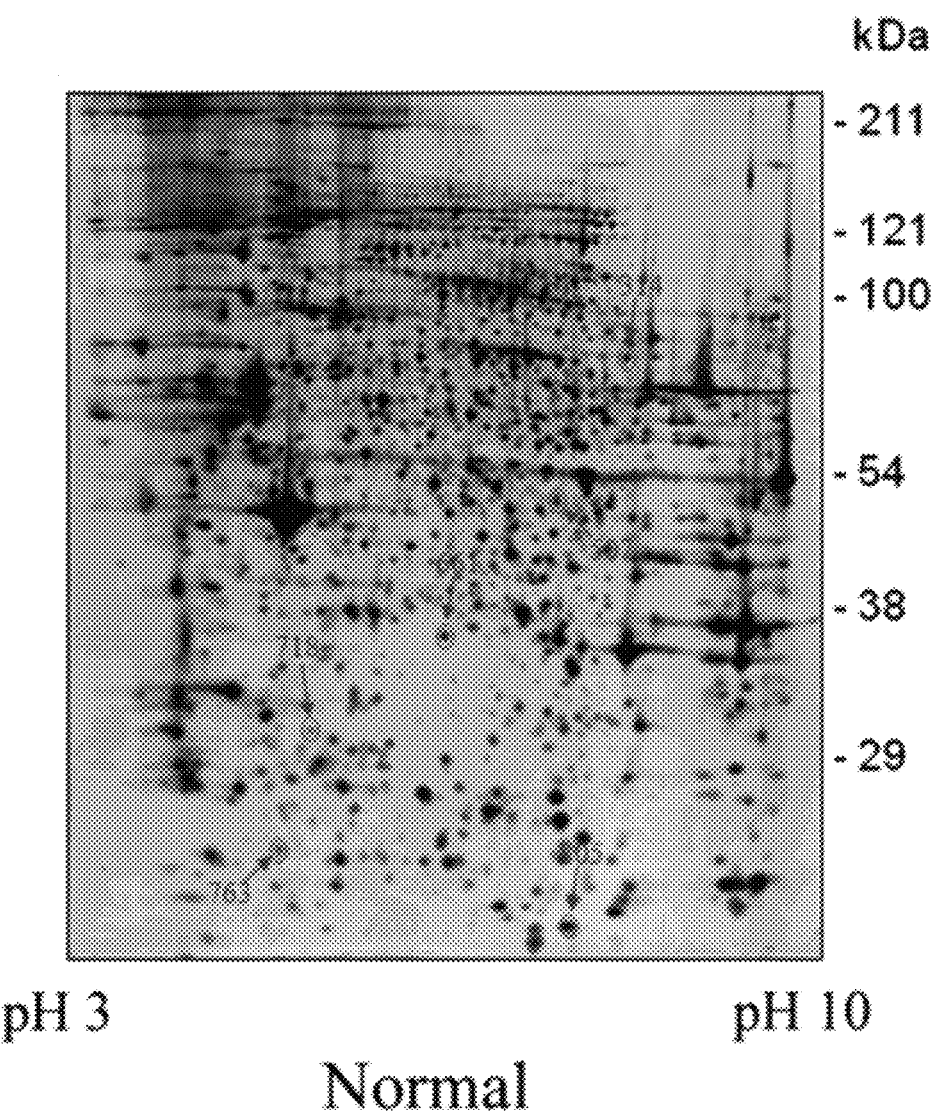
FIG. 1 shows the identification of UCHL1 from type I SMA fibroblast cells. (A)(B) The 2D electrophoresis gels. The differential expression proteins in type I SMA skin fibroblast cells (B) comparing to normals (A) were shown with red number word (arrow). (C) The single spot images of different expression protein spots in 2D electrophoresis gel. (D) UCHL1 expression was up-regulated in type I SMA fibroblast cells. (S: type I SMA patients; N: non-SMA skin fibroblast cells); (E) UCHL1 expression was correlated with SMA severity.
Figure 1:
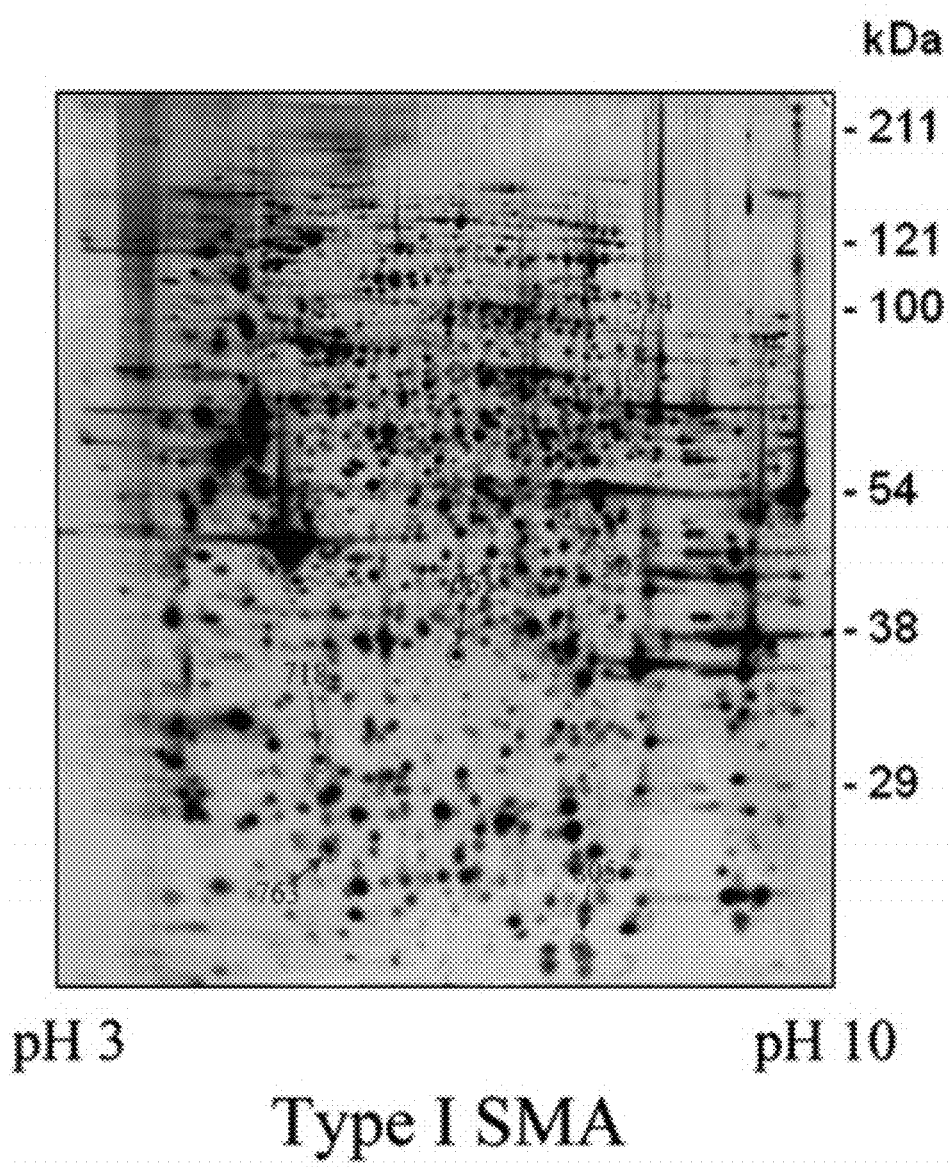
Figure 1:
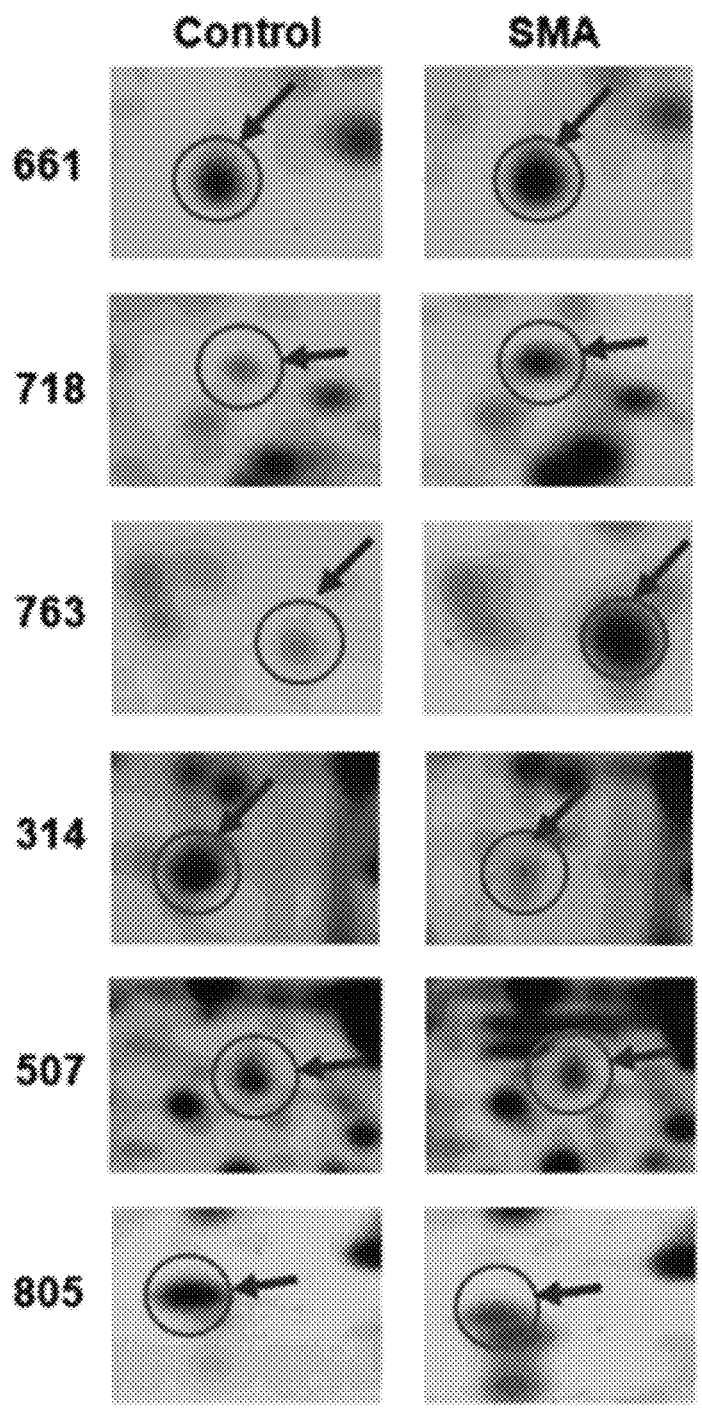

Spinal muscular atrophy (SMA), a lethal hereditary disease caused by homozygous absence of the survival of moto neuron 1 (SMN1) gene, is the leading genetic cause of infant mortality. Its severity directly correlates to the expression level of SMN protein in patients with SMA, but the regulatory mechanisms of SMN protein expression remain incompletely defined. The present invention shows that UCHL1 proteins directly interacted with SMN protein, as determined by immunoprecipitation and immunofluorescence assays in p19 and NSC34 cells. Over-expression of UCHL1 in p19 and NSC34 cells significantly reduced the level of SMN proteins in vivo, and, in fact, purified UCHL1 was shown to be able to enhance, in a dose-dependent manner, the level of ubiquitinated SMN in vitro. Further, inhibition of UCHL1 activity by UCHL1 inhibitor (LDN-57444) increased cellular SMN protein and gems number in the nucleus in NSC34 and SMA skin fibroblasts. The same results were observed in cells with UCHL1-specific knockdown. These results suggested, therefore, that UCHL1 may be a critical regulator in controlling cellular SMN protein turnover, and that it may serve as an attractive therapeutic target for SMA.

DETAILED DESCRIPTION OF THE INVENTION

The present invention relates to a method of regulating the expression level of survival of motor neuron 1 (SMN1) comprising administering to a subject in need thereof a therapeutically effective amount of ubiquitin carboxyl-terminal hydrolase L1 (UCHL1) regulator and a pharmaceutically acceptable carrier, wherein the expression level of survival of motor neuron 1 is protein expression level of survival of motor neuron 1. The protein expression level of survival of motor neuron 1 of the present invention is reduced by ubiquitin carboxyl-terminal hydrolase L1 (UCHL1) regulator, wherein the ubiquitin carboxyl-terminal hydrolase L1 (UCHL1) reduces the expression level of survival of motor neuron 1 by increasing the level of ubiquitinated survival of motor neuron 1. The method of the present invention treats spinal muscular atrophy (SMA).

The present invention also relates to a method of detecting enzyme activity of ubiquitin carboxyl-terminal hydrolase L1 (UCHL1) in human fibroblasts comprising detecting protein expression level of survival of motor neuron 1 (SMN1). The method of the present invention determines therapeutic effect for treatment of spinal muscular atrophy (SMA) by comparing the protein expression level of motor neuron 1 (SMN1) in SMA fibroblasts under treatment with the protein expression level of motor neuron 1 (SMN1) in SMA fibroblasts without treatment, wherein the treatment of spinal muscular atrophy (SMA) is effective when the protein expression level of motor neuron 1 (SMN1) in SMA fibroblasts under treatment is 25% to 87% higher than the protein expression level of motor neuron 1 (SMN1) in SMA fibroblasts without treatment.

EXAMPLES

The examples below are non-limiting and are merely representative of various aspects and features of the present invention.

Example 1

Materials and Methods

Plasmids and Chemicals

UCHL1 full-length cDNA (accession number NM_004181) was obtained from Open Biosystem and sub-cloned with HA or EGFP tagging sequences into pEGFP N3 and pcDNA3 vectors (Invitrogen). The shRNAi plasmid for UCHL1 was constructed by sub-cloning a 52 bp double strand oligonucleotide, in which a UCHL1 22-nt sequence was separated from the reverse complement sequence by a short spacer, TTCAAGAGA, into a human U6 promoter-driven vector (pSM2) (Open Biosystem). MG132 and LDN-54777 (UCHL1 specific inhibitor) were purchased from BIOMOL.

Total Protein Extraction and Two-dimensional Electrophoresis

The total protein extract preparation from type I SMA and normal skin fibroblasts were carried out as previously described (Hsu, S. H. et al. (2005) Cancer Res, 65, 4041-4050). For isoelectric focusing (IEF), methanol/chloroform precipitated samples containing 100 µg proteins were solubilized in the standard rehydration buffer (8 M urea/4% CHAPS/0.5% ampholytes/20 mM DTT). Solubilization was carried out on a vibra-shaker for 2 hours at room temperature. At the end of the incubation, samples were spun for 10 minutes at 16000×g in a micro-centrifuge and transferred to rehydration chambers. The dry IPG strips were allowed to re-swell in rehydration buffer over night before IEF separation. IEF was performed using a two phase protocol: (1) 250 V for 30 minutes and (2) 250-5,500 V fast ramping voltage gradient to accumulate 33,000 total volt-hours. The focused IPG strips were subjected to additional reduction and alkylation treatment before the second dimension SDS-PAGE. The strips were equilibrated for 20 minutes in 25 mM DTT dissolved in 6 M Urea/2% SDS/30% glycerol/50 mM Tris HCl pH 8.8 and then alkylated by incubating with 360 mM acrylamide for 20 minutes in the same buffer. Equilibrated IPG strips were applied to precast Novex 4-12% ZOOM® gels and run at room temperature for 1 hour at 200 V. Silver stained gels were imaged and the total number of spots in individual gels was determined by Phoretix 2D Pro imaging software.

In-gel Digestion

The prepared proteins from two-dimensional (2D) gel were then subjected to in-gel digest procedure as previously described (Hsu, S. H. et al. (2005) Cancer Res, 65, 4041-4050). Each gel slice was diced into small pieces (1 mm$^2$) and placed into 0.65 mL siliconized tubes. The tube had the addition of 100 µL lysis buffer (25 mM NH$_4$HCO$_3$/50% CAN) and was vortexed for 10 minutes. After using gel loading pipet tip to extract and discard the supernatant, the gel pieces were dried with speed vacuum to complete dryness. The dried gel pieces were added to 25 µL elution buffer (10 mM DTT in 25 mM NH$_4$HCO$_3$) and after briefly vortexing and spinning, incubated for 1 hour at 56° C. We added trypsin solution to just barely cover the gel pieces to rehydrate the gel pieces on ice or at 4° C. for 10 minutes and added 25 mM NH$_4$HCO$_3$ as needed to cover the gel pieces for incubation at 37° C. for 4 hours to overnight. We transferred the digest solution (aqueous extraction) into a clean 0.65 mL siliconized tube and added 30 µL of 50% ACN/5% formic acid. After vortexing and spinning, the samples were then sonicated for 5 minutes and the supernatants were collected for analysis by LC-MS/MS (Micromass).

Instrumentation

A trapping column (C18 PepMap, 300 µm ID, 5 mm, LC Packings, Sunnyvale, USA) was used for peptide enrichment and desalting. The separation was performed on a Micro-tech Scientific Inc. (Vista, Calif., USA) 10 cm RP C18 nano-LC column (150 µm inner diameter; 375 µm outer diameter; 3 µm particle size). Tandem mass spectra were acquired by a Global Ultima Q-TOF mass spectrometer with a nanospray source (Micromass, Manchester, UK). The system is comprised of three pumps (pumps A, B and C), an autosampler, an inline degasser, a sample cooler, a syringe pump and a switch valve (Lu, C. Y. et al. (2009) J Pharm Biomed Anal, 49, 123-128).

Protein Identification by LC nanoESI-Q-TOF

Peptides from in-solution digestion were trapped by a desalting column and separated by a nano-LC analytical column. The tryptic peptides were then separated by a nano-LC reversed-phase C18 column with a flow rate of 200 L/minute for 60 minutes. Mobile phase B (from pump B) was 0.1% FA:ACN=95:5 (v/v) and mobile phase C (from pump C) was 0.1% FA:ACN=5:95 (v/v).

After on-line desalting by 0.1% FA (from pump A) for 3 minutes with a flow rate of 30 μL/minute, the switching valve was auto switched to the analytical position. The LC gradient conditions were listed as follows: base on time (t) set at the mobile phase: t=0-3 minutes, hold % C=10; t=3-45 minutes, % C from 10 to 75; t=45-60 minutes, % C from 75 to 10. Finally, the switching valve was auto switched from the analytical position to the desalting position before injecting the next sample.

Immunofluorescence Analysis

The cellular expression localization of UCHL1 and SMN was determined by immunofluorescence as previously described (Hsu, S. H. et al. (2004) *Exp Cell Res*, 294, 185-198). HEK 293 and NSC34 cells were cultured on coverslides pre-coated with poly-L-lysine for 16 hours. After washing with cold PBS, cells were fixed with 2% paraformaldehyde in PBS for 30 minutes on ice, and then the slides were washed with PBS for 30 minutes. Cells were permeabilized with buffer containing 0.2% Triton X-100 and 1% NGS in PBS for 20 minutes on ice, and then the slides were washed with PBS to remove excess detergent. Cells were then incubated in anti-EGFP (or anti-HA) and anti-SMN polyclonal antibody (1:200) for 1 hour at room temperature. After washing cells with PBS for 30 minutes, FITC-conjugated human anti-rabbit and -mouse polyclonal antibody (1:300) was added and the cells were incubated for another 1 hour at room temperature in a humid chamber. Cells were finally counterstained with DAPI to localize the nucleus and observed by confocal microscopy.

Western Blot Analysis

Western blot analysis and immunohistochemical staining were performed as described previously. The primary antibodies used in this study were β-actin (1:2,000, Santa Cruz, 1-19), SMN (1:1,000, Santa Cruz, SC-32313), Gemin 2, Gemin 3 and Gemin 5 polyclonal antibody (1:200, Santa Cruz), UCHL1 monoclonal antibodies (1:2,000, Calbiochem.), HA-tag (1:2,000, Sigma), FITC-conjugated anti-mouse, alkaline phosphatase-conjugated anti-rabbit antibodies (1:500, Jackson ImmunoResearch Lab.) and anti-EGFP rabbit polyclonal antibody (1:5,000, produced in-house).

Immunoprecipitation

Immunoprecipitation assays were performed as previously described with some modifications. Cells with endogenous or ectopically expressed UCHL1 were lysed with RIPA buffer containing 0.2% SDS. After sonication, the lysate was diluted with modified RIPA containing 1% NP-40 for immunoprecipitation. Anti-UCHL1 or anti-SMN antibodies were used to immunoprecipitate the protein. The re-suspended IP complexes were then analyzed by Western blot.

In vitro Ubiquitination

UCHL1 was subcloned into pQE30 (Qiagen) expression constructs tagged with RGS-6His and over-expressed UCHL1 was then purified with Ni-NTA column according to manufacture's standard procedure. Purified RGS-6His UCHL1 and SMN immunoprecipitate from HEK 293 cells were mixed in ubiquitination interaction buffer (50 mM Tris-HCl, pH 7.5, 5 mM $MgCl_2$, 1 mM ATP, 10 mM creatine phosphate, 4 U/mL creatine kinase, ubiquitin monomer and 2.5 mM DTT) and incubated at 30° C. for 2 hours. After SDS-PAGE, the membrane was incubated with anti-RGS-6His (Qiagen) or anti-ubiquitin (P4D1; Santa Cruz) monoclonal antibodies.

Statistical Analysis

The quantitative results in this study are shown as means±S.D. Statistical significance of two-way difference was assessed by Student's t-test.

Example 2

Proteomics Approach Identified Differential Expression of UCHL1 in SMA Fibroblasts To identify cellular targets regulating the expression of SMN, the present invention initially utilized a proteomics approach combining 2D electrophoresis and LC-MS/MS, wherein the total proteins extracted from type I SMA patients and normal skin fibroblast cells were compared. As shown in FIGS. 1A and 1B, the total target proteins (arrow) picked by computer were thirty eight proteins (nineteen of them were up-regulated and fifteen were down-regulated). All of them were identified by the protein ID with LC-MS/MS and are shown in Supplemental Table 1. Among them, six of which (Table 1) were further analyzed in additional SMA skin fibroblast cells (FIGS. 1A, 1B and 1C for representation). The target protein labeled with number 763 in FIGS. 1A, 1B and 1C was identified as ubiquitin carboxy-terminal hydrolase L1 (UCHL1), an enzyme participating in cellular protein degradation. As shown in FIGS. 1D and 1E, the differential expression of UCHL1 was further demonstrated in skin fibroblasts from SMA patients with different phenotypes by Western blot analysis. The UCHL1 expression level was up-regulated in skin fibroblasts of three independent type 1 SMA patients compared to normal fibroblasts (FIG. 1D). Further, FIG. 1E showed that UCHL1 expression level was increased concomitantly with the SMA severity, but other proteins were not. These results, together with the known function of UCHL1 in ubiquitination process, may thus suggest its candidacy as a regulator in controlling SMN expression.

TABLE 1

Identification of differential expresion proteins ID by 2D coupling to LC-MS/MS analysis.

| Spot# | Accession no.* | No.[b] | Entry name[a] | Protein name[a] | Mass (kDa) | pI | Cellular functions[a] |
|---|---|---|---|---|---|---|---|
| S1 763 | P09936 | 3/3 | UCHL1_HUMAN | Ubiquitin carboxy-terminal hydrolase L1 | 24.8 | 5.33 | Ubiquitin-protein hydrolase involved both in the processing of ubiquitin precursors and of ubiquitinated proteins |
| S2 718 | Q9UL46 | 3/3 | PSME2_HUMAN | Proteosome activator complex subunit 2 | 27.4 | 5.44 | Implicated in immunoproteasome assembly and required for efficient antigen processing |
| S3 661 | Q00487 | 3/3 | PSDE_HUMAN | 26S proteasome non-ATPase regulatory subunit 14 | 34.6 | 6.06 | Acts as a regulatory subunit of the 26 S proteasome which is involved in the ATP-dependent degradation of ubiquitinated proteins |

TABLE 1-continued

Identification of differential expresion proteins ID by 2D coupling to LC-MS/MS analysis.

| Spot# | Accession no.* | No.[b] | Entry name[a] | Protein name[a] | Mass (kDa) | pI | Cellular functions[a] |
|---|---|---|---|---|---|---|---|
| N1 507 | Q14240 | 3/3 | IF4A2_HUMAN | Eukaryotic initiation factor 4A-II | 46.4 | 5.33 | ATP-dependent RNA helicase which is a subunit of the eIF4F complex involved in cap recognition and is required for mRNA binding to ribosome |
| N2 314 | P49748 | 3/3 | ACADV_HUMAN | Very long-chain acyl-CoA dehydrogenase mitochondrial | 70.4 | 7.74 | Active toward esters of long-chain and very long-chain fatty acids |
| N3 805 | P02511 | 3/3 | CRYAB_HUMAN | Alpha-crystallin B chain | 20.2 | 6.76 | May contribute to the transparency and refractive index of the lens |

*Spot number corresponds to the labels in FIG. I.
[a]Obtained from http://beta.uniprot.org.
[b]No. indicates the number of patients in which the changes was observed.

Example 3

UCHL1 Interacted with SMN Protein in p19 and NSC34 Cells

In order to determine whether SMN was regulated by UCHL1 or not, the interactive relationship between SMN and UCHL1 was investigated. The SMN and UCHL1 protein complexes were specifically immuno-precipitated from HEK 293 and NSC34 cells with anti-SMN and UCHL1 antibodies. FIG. 2A showed that the SMN protein was immuno-precipitated with anti-SMN antibody and the UCHL1 protein was also found in SMN immuno-precipitate. Further, in UCHL1 immuno-precipitate, the UCHL1 could be detected with anti-UCHL1 antibody and SMN protein was also detected in the UCHL1 immuno-precipitate (FIG. 2B). The interaction between SMN and UCHL1 was further observed by immuno-fluorescence staining in NSC34 cells. FIG. 2C showed that most of the SMN protein (green) and UCHL1 (red) were co-localized (yellow) in the cytoplasm of NSC34 cells.

Example 4

UCHL1 Ubiquitinated SMN Protein In Vitro and In Vivo

Figure 3:
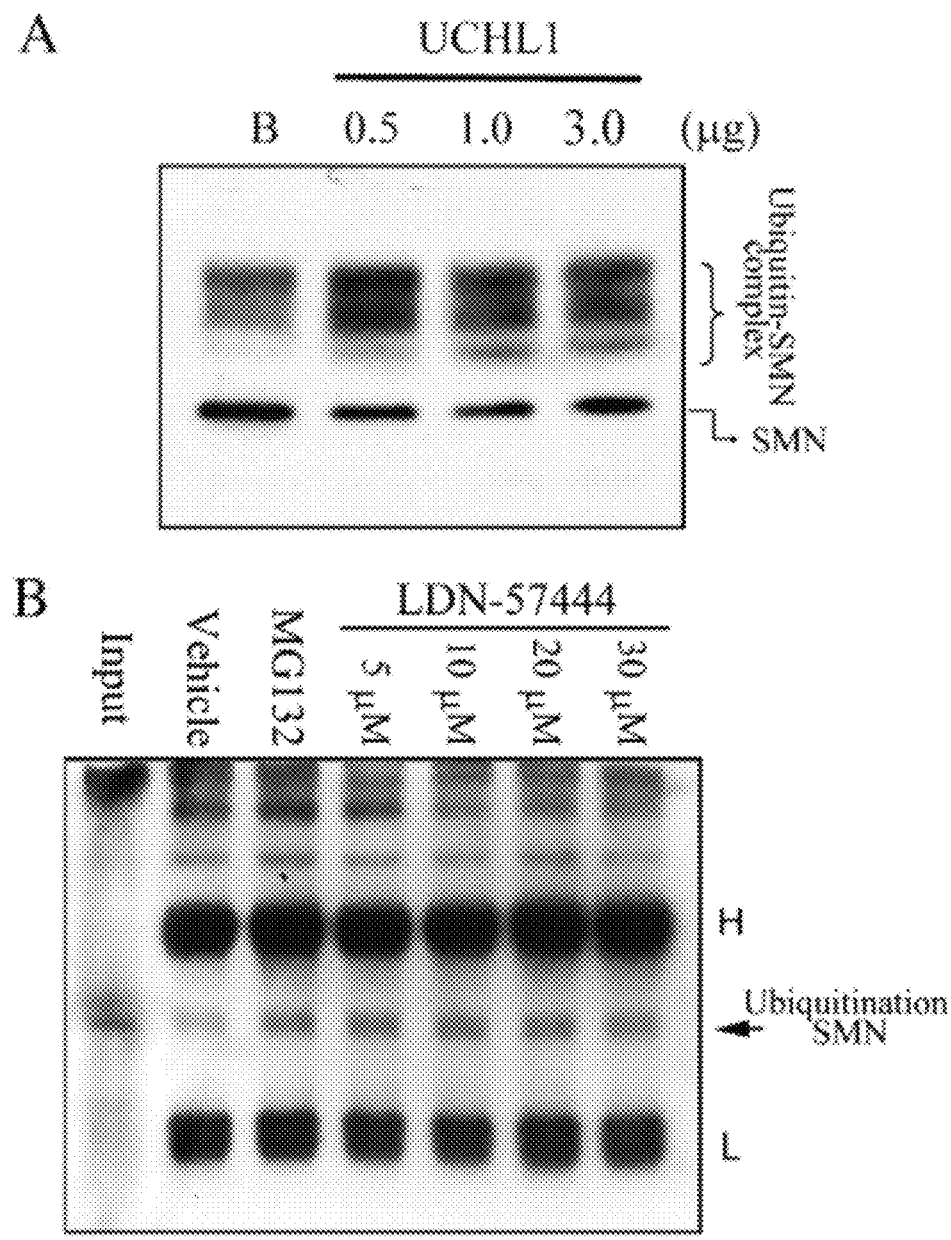
FIG. 3 shows the UCHL1 transferred ubiquitin to SMN protein in vitro and in vivo. (A) In vitro ubiquitination assay. UCHL1 was tagged with RGS-His6 and purified from SG 13009 strain *E. coli.* (B) UCHL1 inhibitor, LDN-57444, inhibited cellular ubiquitination of SMN. Ubiquitinated SMN proteins were immuno-precipitated with anti-SMN antibody and blotted with anti-ubiquitin antibody. H, heavy chain; L, light chain; "*", $p<0.001$.

Next, to determine the functional significance of this interaction, purified UCHL1 tagged with 6×His was co-incubated with SMN immunoprecipitate and in vitro ubiquitination assay was performed. FIG. 3A showed that the level of ubiquitinated SMN protein was increased as the concentration of UCHL1 increased, suggesting that UCHL1 may have an ubiquitin ligase function instead of serving as an ubiquitin hydrolase. The ubiquitination function of UCHL1 was further demonstrated in NSC34 cells in vivo treated with UCHL1 specific inhibitor, LDN-57444. The SMN protein complex was immunoprecipitated from total cell extract treated with different concentrations of UCHL1 inhibitor and the level of ubiquitinated SMN was determined by the use of anti-ubiquitin antibody. As noted in FIG. 3B, the level of ubiquitinated SMN protein was increased when the cells were treated with UCHL1 inhibitor (FIG. 3B), and showed the same enhancement in cells treated with a proteasome inhibitor, MG132. These results suggest, therefore, that SMN protein is a cellular target for ubiquitination by UCHL1, resulting in its degradation in NSC34 cells.

Example 5

UCHL1 Over-expression Decreased Cellular SMN Level

Figure 4:
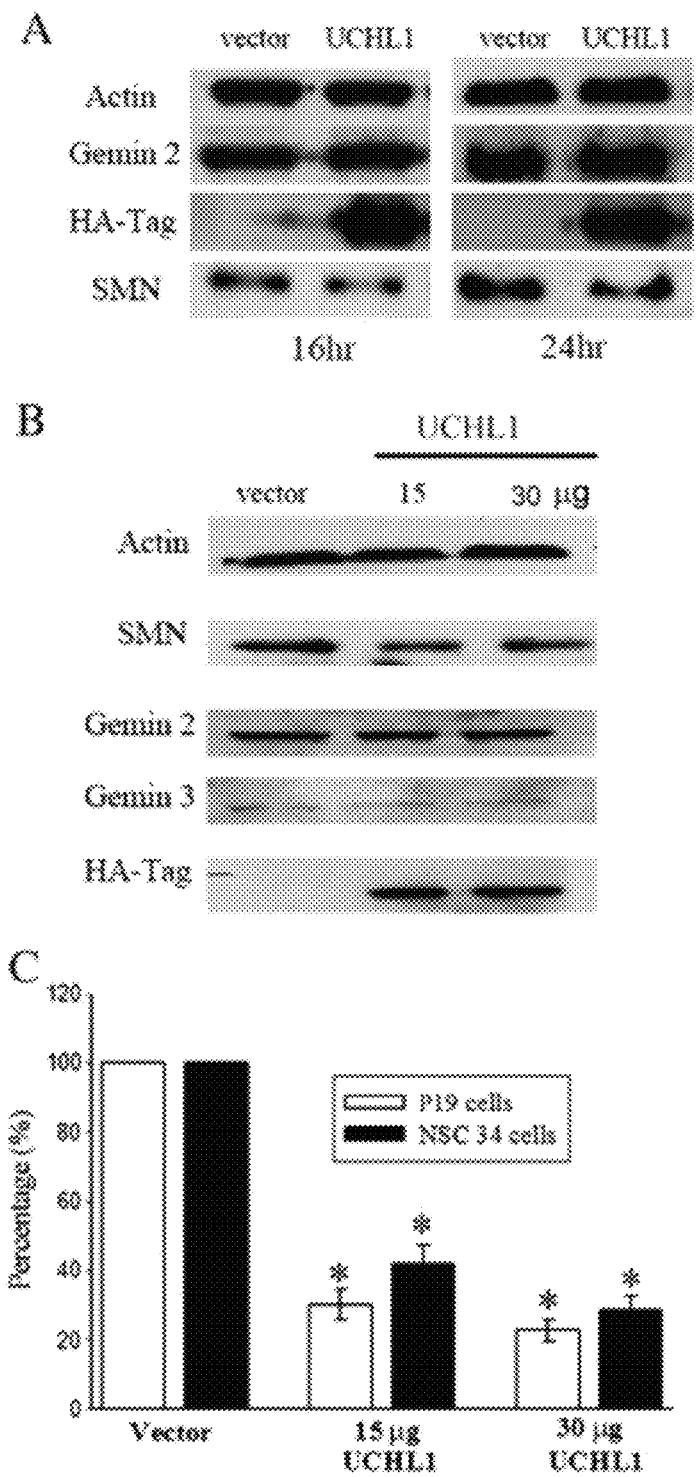
FIG. 4 shows that Over-expression of UCHL1 decreases cellular SMN level. (A) HA-tagged UCHL1 protein was transfected into p19 cell. (B) HA-tagged UCHL1 protein was transfected into NSC34 cells. (C) The inhibition effect of over-expressed UCHL1 in p19 and NSC34 cells.
Figure 5:
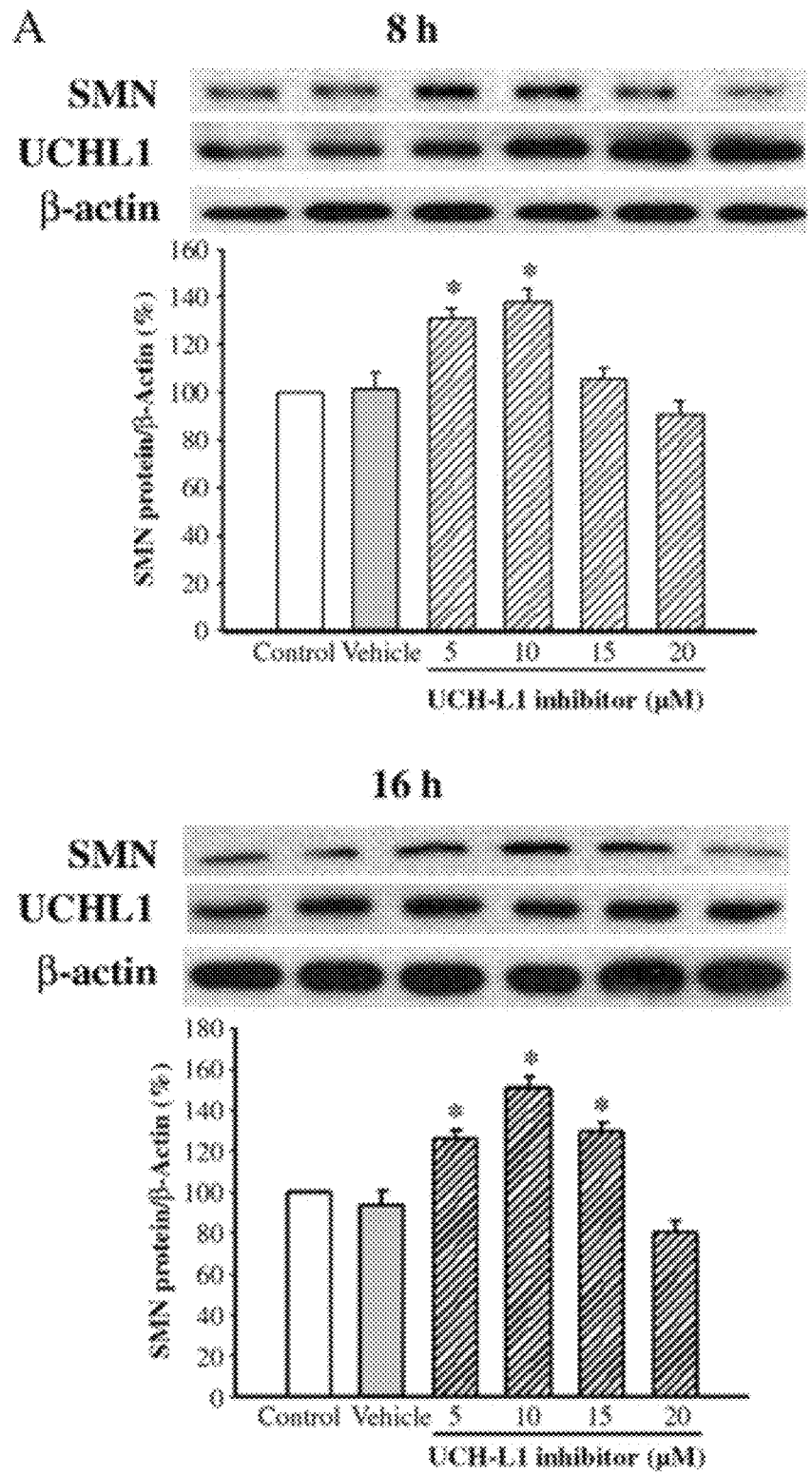
FIG. 5 shows that UCHL1 inhibitor, LDN-57444, increases cellular SMN level in NSC34 cells. (A)(B) LDN-57444 increased cellular SMN protein at different treated time in NSC34 cells. (A) Treated time 8 and 16 hours and (B) treated time 24 and 48 hours. (C) The up-regulation effects of LDN-57444 on cellular SMN protein at different treatment time. (*, $p<0.01$) (D) The SMN protein expression level was increased after UCHL1 shRNAi transfection in NSC34 cells. (E) LDN-57444 increased nuclear gems in NSC34 cells.
Figure 5:
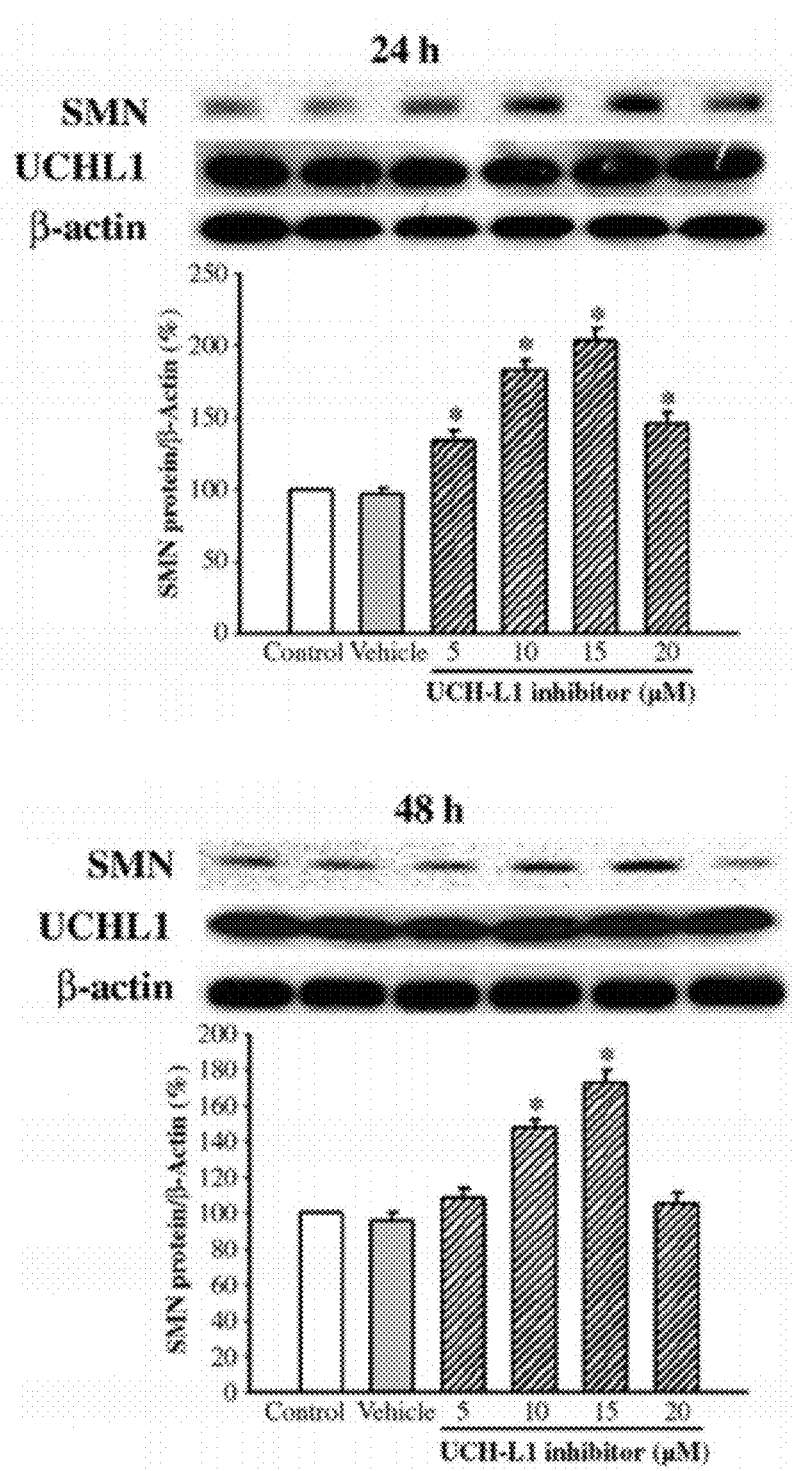
Figure 5:
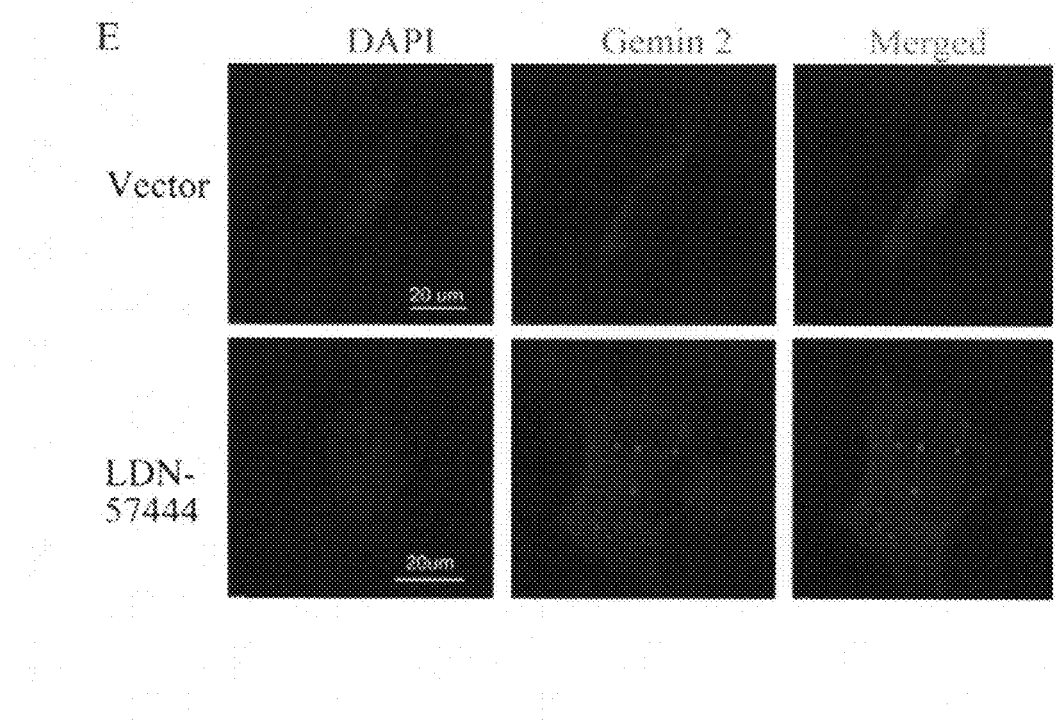

The cellular function of UCHL1 on SMN protein was further characterized with an over-expression assay. The UCHL1 was tagged with HA tag and over expressed in HEK293, p19 and NSC34 cells to evaluate the cellular function. FIG. 4A showed that UCHL1 expression level was determined with anti-HA antibody and cellular SMN protein was decreased inversely to UCHL1 transfection time (24>16 hours), but not Gemin 2. The same result was observed in p19 cells (FIG. 4B), although the decreased level of SMN protein mediated by UCHL1 was not in parallel with the increased amounts of UCHL1 transfection plasmid (FIGS. 4B and 4C). The regulatory effect of UCHL1 was also confirmed with UCHL1 specific inhibitor (FIGS. 5A and 5B). SMN protein could effectively elevate expression level at 5 µM after LDN-57444 treatment for 8 (38%), 16 (42%), 24 (43%) and 48 (46%) hours compared to the vehicle group (FIGS. 5A and 5B). Furthermore, the concentration at 10 µM LDN-57444 showed higher efficiency in causing SMN protein increase at 8 (40%), 16 (56%), 24 (83%), 48 (53%) hours treatment (FIG. 5C). High dosage (15 µM) of UCHL1 inhibitor showed a time delay increase in SMN protein level until 16 hours.

Example 6

Down-regulated UCHL1 by Specific Inhibitor or shRNAi Increased Cellular SMN Level and Function In additional to the use of specific UCHL1 inhibitor, the specific shRNAi constructs for UCHL1 were also used to monitor the regulatory effects of UCHL1 on SMN protein. FIG. 5D showed that three UCHL1 shRNAi constructs were used to knockdown the protein expression in NSC34 cells. The knockdown efficiency of these shRNAi constructs to UCHL1 was 25, 70 and 47% of vector control and the SMN protein was increased 32, 46 and 47% (FIG. 5D). The other proteins (Gemin 2, 3 and 5) did not show any difference after shRNAi treatment, suggesting that the knockdown approach did not have off-target effects (FIG. 5D). The cellular function of elevated SMN was also examined with nucleus gems by immuno-fluorescence staining (FIG. 5E). The nucleus gems stained with anti-Gemin 2 antibody were counted for one hundred NSC34 cells treated with vehicle or LDN-57444 for 24 hours and 48 hours. As shown in Table 2, the gems number per one hundred cells in LDN-57444 (10 µM) comparing to vehicle were increased 2.25 fold (63±4.87 to 142±7.55) after treatment for 24 hours and 2.54 fold after treatment for 48 hours. The result showed increased SMN protein by LDN-57444 could elevate SMN cellular function.

TABLE 2

Total number of nucleus gems per 100 cells after LDN-57444 treatment on NSC-34 cells.

|  | Control | 10 μmol/l | 20 μmol/l |
|---|---|---|---|
| 24 h | 63 ± 4.87 | 142 ± 7.55* | 189 ± 10.72* |
| 48 h[a] | 76 ± 4.18 | 164 ± 8.50* | 193 ± 10.21* |

[a]To replace medium and LDN-57444 each day.
*$p < 0.05$ comparing to vehicle. Each experiment was performed at least 3 times.

Example 7

Figure 6:
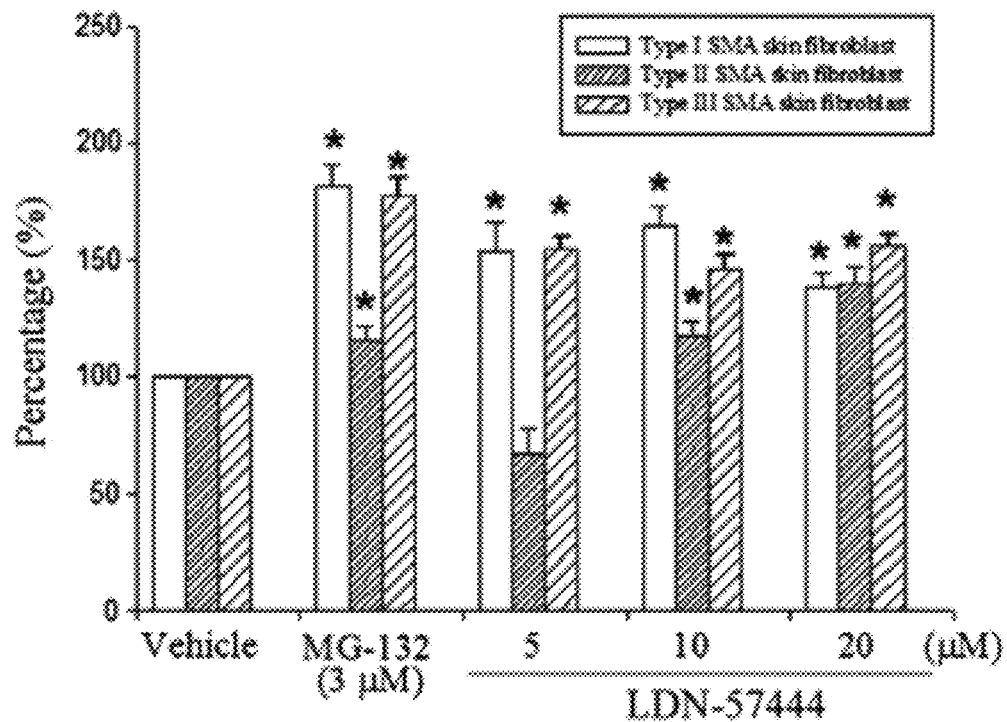
FIG. 6 shows that LDN-57444 treatment increases cellular SMN protein level on SMA patients' skin fibroblast cells. (A) LDN-57444 increased cellular SMN protein level in type I, II and III SMA skin fibroblast cells. (MG132, positive control) (B) The up-regulation effects of LDN-57444 on SMA patients skin fibroblast cells, "*", $p<0.001$.

UCHL1 Inhibitor Increased Cellular SMN Protein Level in Type II and III SMA Skin Fibroblast In order to investigate the possibility of therapeutic application, the UCHL1 specific inhibitor was also applied to the SMA patients' skin fibroblast cells. Type II and type III SMA skin fibroblast cells were treated with MG132, a proteasome inhibitor, and LDN-57444. FIG. 6A showed that the UCHL1 inhibitor as MG132 could inhibit the SMN protein degradation and increased cellular SMN protein level in type I (52-62%) and III (72-87%) SMA skin fibroblast cells, but were less effective in type II (31-38%), possibly because of originally lower individual SMN protein expression (FIG. 6B).

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of increasing the expression level of survival of motor neuron 1(SMN1) in a subject suffered from a spinal muscular atrophy (SMA), comprising administering to the subject an effective amount of ubiquitin carboxyl-terminal hydrolase L1 (UCHL1) inhibitor and a pharmaceutically acceptable carrier;
   wherein the expression level of SMN1 is up-regulated when the UCHL1 inhibitor decreases expression level of UCHL1.

2. The method of claim 1, wherein the expression level of survival of motor neuron 1 is protein expression level of survival of motor neuron 1.

3. The method of claim 1, wherein the ubiquitin carboxyl-terminal hydrolase L1(UCHL1) reduces the expression level of survival of motor neuron 1 by increasing the level of ubiquitinated survival of motor neuron 1.

* * * * *